(12) United States Patent
Gu

(10) Patent No.: US 7,834,056 B2
(45) Date of Patent: Nov. 16, 2010

(54) PHARMACEUTICAL COMPOSITION FOR GOUT

(76) Inventor: Shuhua Gu, 17F-1704 Jiaxin Bldg. A, 18 Hengshan Rd., New District, Changzhou, Jiangsu Province (CN) 213022

( * ) Notice: Subject to any disclaimer, the term of this patent is extended or adjusted under 35 U.S.C. 154(b) by 344 days.

(21) Appl. No.: 11/879,882

(22) Filed: Jul. 18, 2007

(65) Prior Publication Data

US 2008/0249168 A1 Oct. 9, 2008

(51) Int. Cl.
- *A01N 37/02* (2006.01)
- *A01N 37/12* (2006.01)
- *A01N 37/44* (2006.01)
- *A01N 37/30* (2006.01)
- *A61K 31/22* (2006.01)
- *A61K 31/205* (2006.01)

(52) U.S. Cl. .................. 514/546; 514/551; 514/556
(58) Field of Classification Search .................. 514/546, 514/551, 556
See application file for complete search history.

(56) References Cited

U.S. PATENT DOCUMENTS

| 2004/0242491 A1 | 12/2004 | Chang |
| 2006/0062859 A1 | 3/2006 | Blum et al. |

FOREIGN PATENT DOCUMENTS

| EP | 1762232 | 3/2007 |
| JP | 2006223224 | 8/2006 |
| JP | 2006347935 | 12/2006 |
| WO | WO9622774 | 8/1996 |
| WO | WO 00/27386 | 5/2000 |
| WO | WO0048636 | 8/2000 |
| WO | WO0122943 | 4/2001 |
| WO | WO0168534 | 9/2001 |
| WO | WO03068267 | 8/2003 |
| WO | WO2005023305 | 3/2005 |
| WO | WO2006054629 | 5/2006 |
| WO | WO2006087997 | 8/2006 |
| WO | WO2006105912 | 10/2006 |
| WO | WO2006105913 | 10/2006 |
| WO | WO2007059515 | 5/2007 |

OTHER PUBLICATIONS

Lonza. L-carnitine vs. D-Carnitine. Published Online Mar. 2006, L-carnitine, p. 1.*
Harris et al. American Academy of Family Physicians. Feb. 1999, pp. 1-16.*
Dupond et al, "Exercise-induced enzymatic myopathies with normal creatinine kinase levels at rest", Abstract in English, La Presse Medicale vol. 21, No. 21, pp. 974-978 (1992).
Fox, "Adenosine triphospate degradation in specific disease", The J. of Lab. and Clinical Medicine vol. 106, No. 2, pp. 101-110 (1985).
Östman-Smith et al., "Dilated cardiomyopathy due to type II X-linked 3-methylglutaconic aciduria: successful treatment with pantothenic acid", Br. Heart J. 72, pp. 349-353 (1994).
Röschinger et al., "Carnitine-acylcarnitine translocase deficiency: metabolic consequences of an impaired mitochondrial carnitine cycle", Clinica Chimica Acta 298, pp. 55-68 (2000).
Verma "Persistent Hyperinsulinemic Hypoglycemia of Infancy", Perinatology vol. 4, No. 1, pp. 43-49 (2002).
European Search Report for appl. No. 08714929.0-2123, mailed Mar. 17, 2010, 7 pgs.
Loots et al., "Acetyl-L-carnitine prevents total body hydroxyl free radical and uric acid production induced by 1-methyl-4-phenyl-1,2,3,6-tetrahydropyridine (MPTP) in the rat", Life Sciences 75, pp. 1243-1253 (2004).
Rauchova et al., "The effect of chronic L-carnitine treatment on blood pressure and plasma lipids in spontaneously hypertensive rats", EU J. of Pharmacology 342 pp. 235-239 (1998).
Volek et al., "L-Carnitine L-tartrate supplementation favorably affects markers of recovery from exercise stress", Am. J. Physiol Endocrinol Metab 282, pp. E474-E482 (2002).

* cited by examiner

*Primary Examiner*—Sreeni Padmanabhan
*Assistant Examiner*—Samira Jean-Louis
(74) *Attorney, Agent, or Firm*—Squire Sanders & Dempsey, LLP

(57) ABSTRACT

A composition for hyperuricemia disease or a related disorder, use thereof and method of using thereof are provided.

22 Claims, No Drawings

PHARMACEUTICAL COMPOSITION FOR GOUT

CROSS-REFERENCE TO RELATED APPLICATION

This application claims priority to Chinese Application No. 200710021408.7, filed on Apr. 6, 2007, the teaching of which is incorporated herein in its entirety by reference.

BACKGROUND OF THE INVENTION

1. Field of the Invention

This invention relates to a pharmaceutical composition of Levocarnitine (L-carnitine) or its derivatives, and its use for treating hyperuricemia and any a related disorder.

2. Description of the Background

Hyperuricemia (male: serum uric acid (SUA)≧420 mmol/L, female: SUA≧360 mmol/L) and gout is caused by purine metabolic disorder, The activity of the purine metabolic enzyme either congenital or acquired defect, which cause the uric acid either excess, insufficient or either way, cause the uric acid of blood plasma out of the saturation; The SUA slat educed and crystallized in joints, connective tissue and kidney result in the gout episode. The natural progression and clinical manifestations of gout is includes: 1. none symptoms hyperuricemia state; 2. acute onset of gouty arthritis; 3. intermission of gout 4. chronic arthritis of gouty tophus.

The primary hyperuricemia is fewer clinically, recently due to improvement of nutritional status, lengthening of average life expectancy, and people's attention of this disease etc reason, the incidence has been increasing gradually. Prevalence has been increasing with age, particularly in males, fewer in females, which occur more after menopause. Cases reports abroad have shown it related with family history, most of them autosomal recessive inheritances. It happens more in brainworkers and who has favorable economic status; analysis of risk factor indicated that the hyperuricemia in females, have correlation with age, body mass index (BMI), blood inosine, erythrocyte sedimentation rate, while has no correlation with cholesterol and triglyceride (TG); The SUA levels of males have significant correlation with BMI and blood inosine. Epidemiological reports in Spain indicated the rate of hyperuricemia patients with cardiovascular disease and other risk factors are increasing related with age. Multiple regression analysis results suggested that glucose, adiposity and hyperuricemia, ware significantly related to each other; And also related to hypercholesterolemia, hypertension and smoking.

Either primary or secondary hyperuricemia, except a few caused by drugs, most of them lack the treating with pathogeny, so there is not a radical cure. There are four intentions for clinical treatment: 1. to terminate the acute arthritis episode; 2. to prevent arthritis recrudesce; 3. to correct the hyperuricemia, prevent and cure urate deposits in kidneys, joints and so on to cause the complications 4. to prevent and cure urate nephrolithiasis formation.

The treating of gouty arthritis includes: 1) Acute paroxysm stage: colchicines, non-steroidal anti-inflammatory drugs, adrenocorticotropic hormone (ACTH) and prednisone; 2) drugs for reduce serum uric acid: included two kinds of drugs as uricosuric agents and uric acid synthesis inhibitions.

The commonly used uricosuric agents (via inhibition of renal tubular reabsorption of uric acid) are: (1) Probenecid; (2) Sulfinpyrazone; (3) Benzbromarone. During administration of uricosuric agents, orally taking sodium bicarbonate 3-6 g/day to alkalify the urine, liquid retention amount needs keeping on more than 2000 ml a day for advantages in excreted of uric acid.

Uric acid syntheses inhibition agents: at present only allopurinol is available (can inhibit the xanthine oxidase, result in the hypoxanthine and xanthine can't be transformed to uric acid).

It was found that those two kinds of drugs without function of anti-inflammatory and analgesic, and during medication they may mobilize the uric acid into the blood circulation, and induce the acute arthritis attack, so they are not recommended to use at acute paroxysm stage. Selection of agents for treating gout often based on renal function and the quantity of 24 hours uric acid excreted in clinic. If the quantity is below 4.8 mmol/day (800 mg/day), chose uricosuric; if the renal function is declined and the quantity of uric acid excreted above 4.8 mmol/day, chose the drugs for uric acid syntheses inhibitor; if the patient has significantly increased quantity of uric acid excreted and gouty tophus formation, combined the both therapies mentioned above are recommended.

However, all therapies mentioned above aren't etiological treatment. The anti-hyperuricemia agents all have different side effect or toxicity, for example, the drugs for excrete uric acid can cause the crystallization of urate deposition in the urethra, lead to the renal dysfunction and renal colic; uricase inhibitor, allopurinol also myelosuppression, hepatic lesion, dermological toxicity and side effect etc. Therefore, it is necessary to find an effective and relative safer medical composition for treatment of hyperuricemia and related disease.

SUMMARY OF THE INVENTION

Provided herein is a composition comprising an active ingredient selected from L-carnitine, derivatives of L-carnitine, pharmaceutically acceptable salt of L-carnitine, or combinations thereof and optionally a pharmaceutically acceptable carrier. The composition is effective for treating or preventing a hyperuricemia disease or a related disorder. The hyperuricemia disease can be a primary hyperuricemia disease or a secondary hyperuricemia disease. In some embodiments, the hyperuricemia disease is gout. The hyperuricemia related disease can be any hyperuricemia related disorder. In some embodiments, the hyperuricemia related disorder is gouty arthritis.

The derivative of L-carnitine can be any pharmaceutically acceptable derivative of L-carnitine. In some embodiments, the derivative can be selected from acetyl L-carnitine, propionyl L-carnitine, pharmaceutically acceptable salts thereof, or combinations thereof.

The pharmaceutically acceptable salt of L-carnitine can be any pharmaceutically acceptable salt of L-carnitine. In some embodiments, the pharmaceutically acceptable salt can be selected from hydrochloride salt, hydrobromide, iodate, sulfate, nitrate, phosphate, acetate, maleate, fumarate salt, citrate, oxalate, succinate, tartrate, malate, mandelate, trifluoromethyl acetate, pantothenate, methanesulfonate, or toluenesulfanate.

The composition can be in any pharmaceutical formulation. In some embodiments, the formulation can be an oral formulation, or formulation for injection or lyophilized powder injection. In some embodiments, the oral formulation is a liquid, suspension, syrup, troche or capsule.

Generally, the active ingredient is in a dosage effective for hyperuricemia disease or a related disorder. In some embodiments, the active ingredient is in a dosage from about 1-500 mg/Kg weight/per day, e.g., from about 5-300 mg/Kg weight/per day, or from about 10-200 mg/Kg weight/per day.

In some embodiments, the present invention provides a method for treating or preventing hyperuricemia or a related disorder in a mammal. The method comprises administering to the mammal a composition described herein. In some embodiments, the mammal is a human being, e.g., a patient.

DETAILED DESCRIPTION OF THE INVENTION

This invention provides a pharmaceutical composition comprising an active ingredient for treating or preventing hyperuricemia and a related disorder thereof. The active ingredient can be L-carnitine, derivatives thereof, pharmaceutically acceptable salts thereof, or combinations thereof. In some embodiments, the pharmaceutical composition can optionally contain a pharmaceutically acceptable.

The L-carnitine derivatives of this invention can be selected from acetyl L-carnitine, propionyl L-carnitine and their pharmaceutically acceptable salts and pharmaceutically acceptable salts of L-carnitine. Examples of the active ingredient is L-carnitine, acetyl L-carnitine and their pharmaceutically acceptable salts, especially L-carnitine and its pharmaceutically acceptable salts.

The pharmaceutically acceptable salts of this invention include: hydrochloride salt, hydrobromide, iodate, sulfate, nitrate, phosphate, acetate, maleate, fumarate salt, citrate, oxalate, succinate, tartrate, malate, mandelate, trifluoromethyl acetate, pantothenate, methanesulfonate and toluenesulfanate.

The hyperuricemia mentioned in this invention can be caused by all kinds of reasons, including primary and secondary hyperuricemia. An example of hyperuricemia related disorders is gouty arthritis.

An aspect of this invention is to utilize L-carnitine or its derivatives to regulate the fatty acid metabolism to treat or prevent the hyperuricemia (gout), which has gradually increased incidence recently, to overcome the shortcomings of the existent treatment, e.g., that the uricosuric could not be used at acute paroxysm stage, that the allopurinol has side effect etc shortcomes, thus providing a better choice for treating hyperuricemia or a related disorder.

Without being limiting, the mechanism of hyperuricemia is believed to be a secondary pathological change to the metabolic disorders, and is also risk factor to the vital organs such as cardiovascular accident. Therefore, the level of circulating fatty acids increasing when the metabolic is disordered, in addition glucose transporter is declined and the insulin receptor is down regulated, the energy metabolism of myocardium and other important organs are disordered; in order to regulate metabolic balance, a large amount of endogenous carnitine be consumed. Therefore, addition of exogenous L-carnitine accelerates-oxidation of fatty acid; adjust the acyl-ratio of mitochondrial, excrete excessive or none physiological acyl group, eliminate toxic metabolites which caused by the accumulation of acyl; accelerating the oxidation of acetoacetic acid, also working as eliminating and using ketone body effectively; prevent the toxicity of excessive ammonia, working as biological antioxidants free radicals, to maintain the membrane stability, improve animal immunity and the ability of antivirus and anti-stress and so on to treat hyperuricemia.

Pharmaceutical composition of this invention can be used alone or optimally mixed with selected medicinal carrier, excipient or diluent, then deliver to mammals, including humans under the standard of pharmaceutical regulations.

Therefore, on the other hand of the invention, it provided a pharmaceutical preparation for treating hyperuricemia, it contains Levocarnitine or its derivatives or its pharmaceutically acceptable salt mentioned above as active ingredient and optionally one or more pharmaceutically acceptable carriers.

The pharmaceutical preparations of the invention can be administered orally or parenterally. Parenterally administration mainly includes vein injection, such as intravenous administration form and lyophilized powder injection form.

The pharmaceutical preparations of the invention can be the forms of appropriate oral administration, such as tablets, sustained-release tablets, capsules, solutions, suspension or syrup; Optimum choices are solution, suspension, syrup, tablets and capsules.

The drug form of oral delivery of this invention can be obtained by any known method of producing oral delivery of pharmaceutical composition, and the pharmaceutical composition can contain one or more substance selected from sweetening agent, correctional taste agents, colorant and preservative.

Troche contains active extract and mixed with the nontoxic acceptable in pharmaceutical excipient. These excipient such as: inertia thinner as calcium carbonate, sodium carbonate, lactose, calcium phosphate or sodium phosphate; Make-grain and disintegrants such as microcrystalline cellulose, Sodium Carboxymethyl Cellulose, cornstarch or alginic acid, binders such as starch, glutin, Polyvidone or Acacia gum; lube such as magnesium stearate, stearic acid or talcum powder.

Troche can be in a coating or non-coating form, or can be obtained by any known method for making coating for concealing the unpleasant taste and delaying gastrointestinal tract disintegration and absorption, and can extend the effective time period. For example, water-soluble material for concealing the unpleasant taste, such as hydroxypropyl methyl cellulose of hydroxypropyl cellulose or the material for delay releasing time such as ethyl cellulose, cellulose acetate butyrate.

The oral delivery drug form of this invention also can be provided as glutoid capsule, wherein the active extract mixed with the inertia solid thinner such as calcium carbonate, calcium phosphate and kaolin, or can be provided as soft glutin capsule, wherein the active extract mix with the water-soluble carrier such as polyethylene glycol or oil medium such as peanut oil, liquid paraffin or olive oil.

The oral liquid of this invention contain active extract and the mixture excipient or dispersant which can use to prepare the suspension. The excipients include suspension such as sodium carboxymethyl cellulose, methyl cellulose, hydroxypropoxyl methyl cellulose, sodium alginate, polyvidone, tragacanth gum and acacia gum. The dispersant is natural phospholipids such as lecithin, or condensable production of alkylene oxide and fatty acid, such as polyoxyethylene stearates, or the condensable production of alkylene oxide and long chain adipic alcohol as polyoxyethylene cetyl alcohol, or the condensable production of alkylene oxide and the partial ester which deriver from the fat and hexitol, such as polyoxyethane sorbitan monooleate.

The water suspension of this invention also can contain one or more preservatives Such as ethyl p-hydroxybenzoate or propyl p-hydroxy benzoate, one or more colorants, and one or more sweet agents as sucrose, glucide or aspartame.

The syrups of this invention can be prepared with sweet agent, such as glycerin, propanediol, sorbitol and sucrose. The drug forms also include the buffer, preservative, corrective agent, colorant and antioxidant.

The drug form in this invention can be injection form, which is asepsis injection solution or lyophilized powder injection form. The vector or solvent which can be used are water, Ringer's solution, physiological saline, hydrochloric acid, gelatin, mannitol, calcium gluconate, for example.

In some embodiments, the present invention also provides a method for treating and preventing the hyperuricemia in mammals, particularly in human, it is include delivering mammals the pharmaceutical composition of Levocarnitine or its derivatives, alone or in combination with one or more other therapeutic agents.

To deliver human with the pharmaceutical composition of levocarnitine of this invention, the daily dosage usually prescribed by the physician, and the individual dosage related with normal age, weight, gender, response and the symptoms of the patients. Generally, dosage for adult is about 1-500 mg active ingredient/kg weight per day, for example about 5-300 mg active ingredient/kg weight per day.

EXAMPLES

The following examples are only for illustration of the invention and shall not be construed to limit the scope of the present invention.

Example 1

Fifty healthy kunmin Mouse (weight of 18-22 grams, male) were randomly divided into 5 groups, which are positive control group, negative control group, and small (250 mg/kg), medium (500 mg/kg) and large (1000 mg/kg) doses of l-carnitine groups. The solvent for all solutions is 0.5% of sodium carboxymethyl cellulose (CMC—Na), with peritoneal injection in dose of 0.1 ml/10 g for all animals. For positive control group, same dose of 0.5% of CMC—Na solution was injected. One hour after injection of inducer, blood samples were taken from eyeball, stet at room temperature for about one hour, centrifugation at 4000 r.p.m for 10 mins, supernatant was transferred to fresh tube for biochemical test of serum uric acid. Result was presented in table 1.

TABLE 1

The influence of l-carnitine on serum uric acid in hyperuricemia model of Kunmin mouse

| Groups | Dose | Animal Nos | serum uric acid value (X ± S) |
|---|---|---|---|
| Positive control | — | 10 | 128.3 ± 25.87 |
| Negative control | — | 10 | 211.7 ± 63.36▲▲ |
| L-Carnitine small | 250 mg/kg | 10 | 140.6 ± 51.55** |
| L-Carnitine medium | 500 mg/kg | 10 | 130.1 ± 34.8** |
| L-Carnitine large | 1000 mg/kg | 10 | 131.7 ± 24.79** |

▲▲Compare with Positive control group $P < 0.01$
**Compare with negative control group, $P < 0.01$ The result was indicated that L-carnitine in dose at 250-1000 mg/kg reduced serum uric acid level of model animal group significantly.

Example 2

The Influence of L-Carnitine on Serum Uric Acid Level in Normal Kunmin Mouse

Thirty healthy kunmin mouse (weight of 18-22 grams, male) were randomly divided into 3 groups, which are positive control group, negative control group, and l-carnitine (300 mg/k) group. Others method was same as example 1. The result was shown as below:

TABLE 2

The influence of L-carnitine on serum uric acid level in normal kunmin mice

| Groups | Dose | Animal Nos | serum uric acid value (X ± S) |
|---|---|---|---|
| Positive control | — | 10 | 58.0 ± 44.0 |
| Negative control | — | 10 | 109.11 ± 43.82 |
| L-Carnitine | 300 mg/kg | 10 | 76.9 ± 30.77# | compare with normal positive control group, $P > 0.05$

The result above shown that l-carnitine was not affecting uric acid level of normal kunmin mices.

Summary of the Results of Examples 1 and 2

L-carnitine reduced the uric acid level significantly in hyperuricemia model mouse; while it has no effect on uric acid level in normal mouse. The efficacy of the composition described in the present invention is clearly shown in Example 1, where uricase inhibitor oteracil potassium is used as model inducer to induce hyperuricemia in Kunmin mouse, and administered Levocarnitine to observe novel pharmacological effect on the model. The test results shown: when SUA reach normal level (such as the SUA result of the middle-dose group), it will not alter blood uric acid level, even increasing the dose of L-carnitine administered, (another experiment of reducing the dose administrated, same result was obtained), and that this results have been confirmed in example 2 as well. The experiments in Examples 1 and 2 show that Levocarnitine may altered the SUA level by regulating the fatty acid metabolize, maybe redress the pathogeny of hyperuricemia (the metabolic disorder), then have the function of reduce the SUA level.

Example 3

L-Carnitine Oral Solution Preparations

Ingredients:

| L-carnitine | 200 g |
|---|---|
| Ethyl p-Hydroxybenzoate | 1 g |
| Distilled water | add to 1000 ml |

Process of Preparation:

L-carnitine, and ethyl p-hydroxybenzoate were dissolved in 100 ml distilled water (DDW), measured up to 1000 ml with DDW.

Example 4

L-Carnitine Syrup Preparations

Ingredients:

| L-carnitine | 200 g |
|---|---|
| Distilled water | 15 ml |
| Simple syrup | add to 1000 ml |

Process of Preparation:
Dissolving L-carnitine in the distilled water, and adding simple syrup to 1000 ml.

Example 5

L-Carnitine injection

Ingredients:

| | |
|---|---|
| L-carnitine | 200 g |
| Hydrochloric acid (pH regulator) | 20 g |
| Water for injection | add to 1000 ml |

Process of Preparation:

80% water for injection was added as prescribed above to container, then L-carnitine was caused to dissolve in it; the pH to was then adjusted to about 6.0 to 6.2, and the solution was measured up with DDW to 1000 ml. The resultant solution was decolorized with 0.15% active carbon, filtrated with pellucid, and then filtrated with sintered glass filter and membrane filter. The resultant solution is encapsulated under the nitrogen stream, and finally sterilized in 100° C. flowing steam for 15 minutes.

Example 6

L-Carnitine Transfusion Preparations

Ingredients:

| | |
|---|---|
| L-carnitine | 200 g |
| Hydrochloric acid (HCL) | 50 g |
| Water for injection | add to 1000 ml |

Process of Preparation:

Dissolving L-carnitine as prescribed above in the 800 ml water for injection, stirring mixing, and adjusting the pH to around 6.0 with 10% hydrochloric acid, adding some injection water to form a solution, then decolorizing the solution with 0.15% active carbon, the solution is filtrated with pellucid, encapsulated and filled into the 200 ml transfusion bottle under nitrogen. The filled bottle is covered with a lid, packed and sterilized in 100° C. for 30 minutes.

Example 7

Sterilized L-Carnitine for Injection in Freeze-Dried Form Ingredients

| | |
|---|---|
| L-carnitine | 2 g |
| Hydrochloric acid | 50 ml |
| Hydrolyze glutin (filler) | 15 g |
| Mannitol (filler) | 10 mg |
| Calcium gluconate (filler) | 1 mg |
| Cysteine (stabilizer) | 0.5 mg |

Process of Preparation:

Dissolving all the substances above in water for injection, filtrating the resultant solution under the aseptic condition, filling the filtrated solution into ampoules, one ampoule being 5 ml, which is obturated after freeze-drying, and checked to see if there is gas leaking.

Example 8

L-Carnitine Granules (Every Thousand Packs)

Ingredients:

| | |
|---|---|
| L-carnitine | 300 g |
| PVP K30 | 40 g |
| PVPP | 15 g |
| Lactose | 250 g |
| Sucrose | 350 g |
| Citric acid | 20 g |

Process of Preparation:

Filtrating L-carnitine with 80# mesh screen, mixing the filtrated solution with lactose and sucrose uniform, adding PVP K30 solution, forming grains with 14# mesh screen and drying at 70° C. to 80° C., then forming granules with 12# mesh screen, adding PVPP and citric acid and mixing the ingredients to uniform, and packaging.

Example 9

L-Carnitine Troche

Ingredients:

| | |
|---|---|
| L-carnitine | 330 g |
| Starch | 40 g |
| 10% starch solution | 24 g |
| Starch powder | 23 g |
| Magnesium stearate | 3 g |

Process of Preparation:

Filtrating L-carnitine with 80# mesh screen, mixing it with starch to in uniform, adding the 10% starch as prescribed above, then forming grains with 14# mesh screen, drying at 70° C. to 80° C., then forming granules with 12# mesh screen, adding starch powder and mixing all the ingredients in uniform, and finally forming troche.

Example 10

L-Carnitine Sustained Release Tablets

Ingredients (for 1000 Tablets):

| | |
|---|---|
| L-carnitine | 500 g |
| Citric acid | 10 g |
| Ethylcellulose | 220 g |
| Lactose | 80 g |
| Magnesium stearate | 20 g |

Process of Making Tablets

Mixing the L-carnitine, lactose and ethylcellulose in uniform, dissolving citric acid in ethanol as wetting agent, forming granules, drying, forming granules again, adding magnesium stearate and mixing the ingredients well in uniform, and finally forming the tablets.

I claim:

1. A method for treating hyperuricemia disease or a related disorder, comprising applying to a mammal a composition consisting of an active ingredient selected from L-carnitine, derivatives of L-carnitine, pharmaceutically acceptable salts of L-carnitine, or combinations thereof and a pharmaceutically acceptable carrier, wherein the active ingredient is in an amount effective for the hyperuricemia disease.

2. The method of claim 1, wherein the derivative is selected from acetyl L-carnitine, propionyl L-carnitine, pharmaceutically acceptable salts thereof, or combinations thereof.

3. The method of claim 2, wherein the pharmaceutically acceptable salt is selected from hydrochloride salt, hydrobromide, iodate, sulfate, nitrate, phosphate, acetate, maleate, fumarate salt, citrate, oxalate, succinate, tartrate, malate, mandelate, trifluoromethyl acetate, pantothenate, methanesulfonate, or toluenesulfanate.

4. The method of claim 1, wherein the hyperuricemia disease is primary hyperuricemia disease.

5. The method of claim 1, wherein the hyperuricemia disease is a secondary hyperuricemia disease.

6. The method of claim 1, wherein the hyperuricemia disease is gout.

7. The method of claim 1, wherein the hyperuricemia related disease is gouty arthritis.

8. The method of claim 1, wherein the composition is in a formulation selected from an oral formulation, or formulation for injection or lyophilized powder injection.

9. The method of claim 7, wherein the oral formulation is selected from liquid, suspension, syrup, troche and capsule.

10. The method of claim 1, wherein the active ingredient is in a dosage from about 1-500 mg/Kg weight/per day.

11. The method of claim 2, wherein the active ingredient is in a dosage from about 1-500 mg/Kg weight/per day.

12. The method of claim 3, wherein the active ingredient is in a dosage from about 1-500 mg/Kg weight/per day.

13. The method of claim 10, wherein the active ingredient is in a dosage from about 5-300 mg/Kg weight/per day.

14. The method of claim 11, wherein the active ingredient is in a dosage from about 5-300 mg/Kg weight/per day.

15. The method of claim 13, wherein the active ingredient is in a dosage from about 5-300 mg/Kg weight/per day.

16. The method of claim 10, wherein the active ingredient is in a dosage from about 10-200 mg/Kg weight/per day.

17. The method of claim 11, wherein the active ingredient is in a dosage from about 10-200 mg/Kg weight/per day.

18. The method of claim 13, wherein the active ingredient is in a dosage from about 10-200 mg/Kg weight/per day.

19. The method of claim 1, wherein the composition is a formulation selected from an oral formulation, or formulation for injection or lyophilized powder injection; and
wherein the active ingredient is in a dosage of about 1-500 mg/kg weight/per day.

20. The method of claim 1, wherein the hyperuricemia is gout.

21. The method of claim 19, wherein the hyperuricemia is gout.

22. The method of claim 1, wherein the mammal is a human being.

* * * * *